United States Patent
Jang

(10) Patent No.: US 9,445,973 B2
(45) Date of Patent: Sep. 20, 2016

(54) DENTAL FILLING COMPOSITION COMPRISING ZIRCONIA POWDER

(71) Applicant: Sung Wook Jang, Seoul (KR)

(72) Inventor: Sung Wook Jang, Seoul (KR)

(73) Assignee: MARUCHI, Wonju-Si (KR)

( * ) Notice: Subject to any disclaimer, the term of this patent is extended or adjusted under 35 U.S.C. 154(b) by 96 days.

(21) Appl. No.: 14/387,234

(22) PCT Filed: Mar. 19, 2013

(86) PCT No.: PCT/KR2013/002250
§ 371 (c)(1),
(2) Date: Sep. 22, 2014

(87) PCT Pub. No.: WO2013/141579
PCT Pub. Date: Sep. 26, 2013

(65) Prior Publication Data
US 2015/0047531 A1    Feb. 19, 2015

(30) Foreign Application Priority Data

Mar. 20, 2012 (KR) ........................ 10-2012-0028458

(51) Int. Cl.
| | |
|---|---|
| *A61K 6/02* | (2006.01) |
| *A61C 5/00* | (2006.01) |
| *A61K 6/06* | (2006.01) |
| *A61K 6/00* | (2006.01) |

(52) U.S. Cl.
CPC ........... *A61K 6/0681* (2013.01); *A61K 6/0017* (2013.01); *A61K 6/0038* (2013.01); *A61K 6/024* (2013.01); *A61K 6/0606* (2013.01); *A61K 6/0618* (2013.01)

(58) Field of Classification Search
CPC ............ A61K 6/0008; A61K 6/0032; A61K 6/0038; A61K 6/0606; A61K 6/0618; A61K 6/0612; A61K 6/024; A61K 6/06
See application file for complete search history.

(56) References Cited

U.S. PATENT DOCUMENTS

| | | |
|---|---|---|
| 5,415,547 A | 5/1995 | Torabinejad et al. |
| 8,475,811 B2 * | 7/2013 | Yang .................. A61L 24/0015 424/400 |

FOREIGN PATENT DOCUMENTS

EP            1149573 A2    10/2001

OTHER PUBLICATIONS

Korea Intellectual Property Office, PCT International Search Report for PCT application No. PCT/KR2013/002250, Jul. 9, 2013, Korea.

* cited by examiner

*Primary Examiner* — Carol M Koslow

(57) ABSTRACT

A dental filling composition includes zirconia powder, a hydraulic inorganic binding agent, a slightly acidic hardening controller agent and a pozzolan component with respect to the gross weight of the composition. The dental filling composition includes 45% to 85% of zirconia powder with respect to the gross weight of the composition, and includes a minimum quantity of inorganic binding agent, thus exhibiting excellent radio opacity and hardly comprising heavy metals. Therefore, the dental filling composition of the present invention is excellent in biocompatibility, and therefore, can be safely and widely used in various dental filling operations.

11 Claims, 2 Drawing Sheets

DENTAL FILLING COMPOSITION COMPRISING ZIRCONIA POWDER

FIELD OF THE INVENTION

The present invention relates to a dental filling composition comprising zirconia powder and a hydraulic inorganic binder, and more particularly, to a dental filling composition comprising zirconia powder at 45 to 85% with respect to the total weight of the composition, and comprising a minimum amount of an inorganic binder, thus exhibiting good radiopacity and biocompatibility.

BACKGROUND

Recently, there is an increasing tendency to preserve natural teeth as much as possible and tooth filling treatment is being actively implemented, so more and more attention is paid to filling materials used therefor.

An ideal dental filling composition should be excellent in properties such as biocompatibility, bactericidal property, sealing property, stability, workability, injectability and dispersibility, hardening time, capability for enhancing tooth structure, homogeneity, and radiopacity.

In U.S. Pat. No. 5,415,547 issued in 1995, Prof. Mahmoud Torabinejad at Loma Linda University has disclosed a dental filling composition being hardenable under moist conditions, in which bismuth oxide is added at 20 to Portland cement for radiopacity, and a method for using the same. Thereafter, Dentsply Tulsa Dental, Inc. has released a product under a brand name, ProRoot MTA. As the effectiveness of the product is widely known, there have been developed a variety of similar products such as MTA Angelus (from Angelus), OrthoMTA (from BioMTA), BioAggregate (from Verio Dental), Biodentine (from Septodont) and other bioceramic materials.

The above existing dental filling materials mainly consisting of calcium silicate cement are intended to comprise various heavy metals as much as 10 to 30% to have radiocontrast properties. The heavy metals include bismuth oxide, tantalum oxide, tungsten oxide, barium sulfate and the like, and are not preferable in terms of biocompatibility to be used as dental filling materials prone to directly contacting blood vessels and nerves in a human body.

In connection with addressing the above problem, Korean Laid-open Patent Publication No. 10-2011-0070269 discloses a root canal filling material having good radiopacity and biocompatibility, which comprises zirconia beads at 10 to 100 wt %, preferably at 10 to 40 wt %, more preferably at 20 to 25 wt %, and an inorganic binder at 0 to 90 wt %, preferably at 60 to 90 wt %, more preferably at 75 to 80 wt %. In the embodiments of the above publication, a root canal filling material comprising zirconia beads at 20 wt % is suggested.

However, when using the zirconia beads employed in the above prior art, flowability is low due to the large size of the particles, and water-tightness for preventing bacterial invasion is reduced. Further, sufficient radiopacity cannot be achieved if the content of the zirconia beads is 40 wt % or less as in the above preferable range of the content, thus causing a problem that additional heavy metals are required to be added.

Furthermore, when using 70 to 90% of the inorganic binder in the existing dental filling materials like MTA mainly consisting of calcium silicate cement, calcium hydroxide ($CaOH_2$) produced in the hydration process causes a strong alkaline action to have an irritant effect on dental pulp and paradental tissues for a long time.

SUMMARY OF THE INVENTION

In order to solve the problems as described above, one object of the present invention is to provide a dental filling composition having excellent biocompatibility, remarkable water-tightness for preventing bacterial invasion, and good radiopacity, in which zirconia powder is contained in an amount enough to achieve radiopacity suitable for dental filling even without heavy metals, and a hydraulic inorganic binder is used in a minimum amount.

According to one aspect of the invention to achieve the above object, there is provided a dental filling composition comprising amorphous zirconia powder, wherein the composition comprises the following with respect to the total weight thereof:

1) 45 to 85% of zirconia powder;
2) 14 to 54% of a hydraulic inorganic binder;
3) 0.5% or less of weakly acidic maleic acid, citric acid, or tartaric acid as a hardening control agent; and
4) 5% or less of a pozzolan component.

The dental filling composition according to the invention, which comprises zirconia powder at 45 to 85 wt % with respect to the total weight thereof, rarely contains heavy metals and employs a minimum amount of a hydraulic inorganic binder, thus exhibiting excellent biocompatibility, good radiopacity and low micro-leakage. Further, the composition minimizes calcium hydroxide produced in the hydration process, so that calcification is suppressed and less irritation is caused in surrounding tissues. Furthermore, the composition is suitable for clinical use since a weakly acidic material like maleic acid, citric acid, or tartaric acid is used as a hardening control agent to control the reaction rate.

Therefore, the dental filling composition according to the invention may be used in a variety of dental filling treatments such as pulp capping, pulpotomy, retrograde filling, fistula site restoration, and root canal filling.

DETAILED DESCRIPTION OF THE PREFERRED EMBODIMENTS

Figure 1:
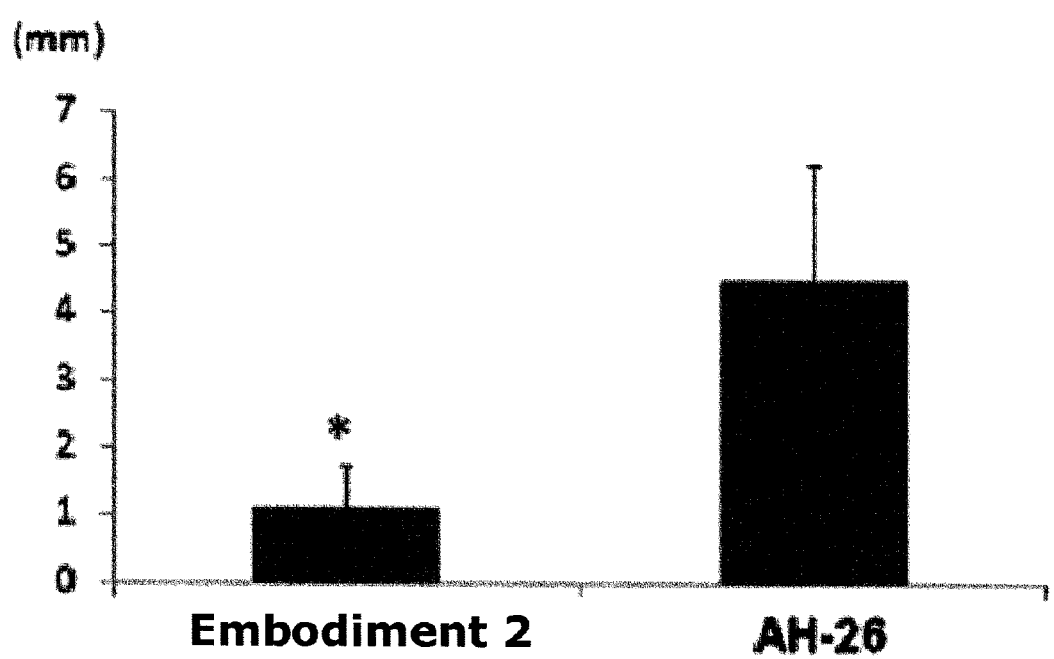
FIG. 1 is a graph comparing the maximum length of micro-leakage in teeth after a composition of Embodiment 2 according to the invention and AH-26 are used as root canal sealers, respectively.

A dental filling composition according to the present invention is characterized in that zirconia powder is used at 45 to 85% with respect to the total weight of the composition in order to achieve good radiopacity and biocompatibility without using heavy metals; the content of a hydraulic inorganic binder is minimized; the workability and water-tightness of the composition is maximized by using a pozollan component; and a weakly acidic hardening control agent is used to control the reaction rate when mixing the composition.

In the following, the present invention will be described in more detail.

(1) Zirconia Powder

Zirconia, which is employed as a main material in the dental filling composition of the invention, is a heat-resistant material with high melting temperature (about 2,700° C.) and has other good material properties such as low thermal conductivity, chemical-resistant stability in a wide range from acidity to alkalinity, low thermal expansion, and wear-resistance based on high strength and high hardness (7.0 or higher on Moh's hardness scale). Further, since Zirconium is an element in Group V of the periodic table and is more biocompatible than titanium, it is employed as a structure to directly contact living tissues such as hip joints and implants.

It is preferable that the zirconia powder employed in the invention has a molecular weight of 123.22 and is amorphous, and that the average grain size thereof is 20 μm or less, depending on the purpose of use. Further, the average grain size is preferably 10 to 20 μm when the dental filling composition of the invention is employed as a base/liner, and is preferably 1 μm or less when the composition is employed as a sealer.

In the present invention, the zirconia powder may be used at 45 to 85% with respect to the total weight of the composition. When the composition is employed as a base, it is appropriate that the powder is preferably used at 45 to 55%, more preferably at 48 to 52% (the weight ratio of the zirconia powder and inorganic binder being about 1:1). Further, when the composition is employed as a sealer for permanent teeth, it is desirable that the powder is preferably used at 60 to 70%, more preferably at 64 to 68% (the weight ratio of the zirconia powder and inorganic binder being about 2:1). Furthermore, when the composition is employed for root canal filling of deciduous teeth, it is desirable that the powder is preferably used at 70 to 85%, more preferably at 73 to 77% (the weight ratio of the zirconia powder and inorganic binder being about 3:1).

If the content of the zirconia powder meets the range of the present invention, the composition has a radiopacity as high as that of an aluminum step wedge having a thickness of 4 mm or greater.

However, the radiopacity is reduced if the content of the zirconia powder is less than 45%, so that heavy metals should be added in order to achieve the radiopacity suitable for dental filling. If the content exceeds 85%, the radiopacity becomes excessively high and a problem of brittleness is caused.

(2) Hydraulic Inorganic Binder

The dental filling composition according to the invention employs calcium silicate cement as the inorganic binder having hydraulic property, and the content thereof is minimized to reduce the amount of highly alkaline calcium hydroxide produced in the hydration process of the calcium silicate cement, so that the calcification of dental pulp is suppressed and less irritation is caused in paradental tissues.

Accordingly, in the present invention, the inorganic binder is used at 14 to 54% with respect to the total weight of the composition. When the composition is employed as a base of which strength is essential, it is appropriate that the binder is preferably used at 44 to 54%, more preferably at 47 to 51% (the weight ratio of the zirconia powder and inorganic binder being about 1:1). Further, when the composition is employed as a sealer for permanent teeth, it is desirable that the binder is preferably used at 29 to 39%, more preferably at 31 to 35% (the weight ratio of the zirconia powder and inorganic binder being about 2:1). Furthermore, when the composition is employed as a root canal filling material for deciduous teeth, it is desirable that the binder is preferably used at 14 to 29%, more preferably at 22 to 26% (the weight ratio of the zirconia powder and inorganic binder being about 3:1).

If the content of the inorganic binder is less than 14%, the toughness and brittleness of the composition are increased, causing a problem that the composition becomes crumbly. If the content exceeds 54%, calcium hydroxide produced in the hydration process causes a strong alkaline action to have an irritant effect on dental pulp and paradental tissues for a long time.

Meanwhile, the average particle size of the existing MTA or calcium silicate cement is excessively large, which disadvantageously causes the composition to have poor flowability and film thickness, and hinders the application thereof to narrow and small complicated portions within teeth. Therefore, it is preferable to address the disadvantages in order to meet the international standards required for dental filling compositions, particularly for root canal fillers or root canal sealers.

Therefore, it is preferable in the present invention to use an inorganic binder having an average grain size of 3 μm or less, in order to produce a product to fill narrow and wet tooth cavities and meet the international standards.

However, as the particles of the inorganic binder become finer, the flowability or film thickness of the composition is enhanced while the reaction rate becomes higher, which disadvantageously causes the composition to be inappropriate for clinical use.

(3) Hardening Control Agent

In order to solve the problems as described above, the present invention employs a hardening control agent which is weakly alkaline and does not deteriorate the physical and chemical properties of raw materials. Examples of the hardening control agent include maleic acid, citric acid and tartaric acid, and citric acid is preferable. Further, it is desirable that the content of the hardening control agent is 0.5% or less, preferably 0.25% or less, with respect to the total weight of the composition.

(4) Pozzolan Component

In order to enhance workability and water-tightness, the composition according to the invention also comprises a pozzolan component, which may be contained at 5% or less, preferably at 3% or less, with respect to the total weight of the composition. Further, for reaction with the pozzolan, the composition may further comprise one or more additives selected from a group consisting of fumed silica, volcanic ash, kaolin, coral powder, and clay silicate.

The composition according to the invention is preferably in powder form.

The above-described composition of the invention may be mixed and applied to teeth requiring to be filled, according to methods well known in the art. Preferably, a method may be employed in which the composition is applied as contained in a conventional thin needle tip (e.g., a Centrix needle tip) insertable in root canals.

The dental filling composition according to the invention comprises zirconia powder and exhibits good radiopacity even without heavy metals. Further, the composition is gradually and completely hardened in narrow and wet environment within teeth, so that bacterial invasion from the outside is prevented. Furthermore, the composition has low micro-leakage and exhibits excellent biocompatibility since calcium hydroxide produced in the hydration process is controlled.

Therefore, the composition according to the invention may be particularly utilized in treatment techniques such as restoring of root perforation (for filling perforation in tooth roots), retro-filling of root ends (for resecting and sealing some parts of inflamed tooth root ends), pulp capping (for applying the composition to injured parts of tooth nerves, which are exposed due to deep caries or accidents, to facilitate recovery and prevent secondary infection), resecting of deciduous teeth (for resecting and sealing some parts of tooth nerves in deciduous teeth having deep caries), and the like.

The present invention will be described below in more detail by way of embodiments. However, these embodiments are merely illustrative of the present invention, which is not limited thereto.

Embodiments 1 to 4

Preparing Dental Filling Composition Comprising Zirconia Powder

Amorphous zirconia powder having an average grain size of 0.4 μm, calcium silicate cement having an average grain size of 1.5 μm, citric acid and pozzolan were mixed such that they are contained as shown in TABLE 1 with respect to the total weight of the composition comprising the zirconia powder, and stirred sufficiently to mix them uniformly. Thereby, the composition comprising the amorphous zirconia powder was prepared.

TABLE 1

| | Zirconia powder (wt %) | Calcium silicate cement (wt %) | Citric acid (wt %) | Pozzolan (wt %) | Zirconia powder to Calcium silicate cement |
|---|---|---|---|---|---|
| Embodiment 1 | 49.75 | 47.7 | 0.25 | 2.3 | About 1:1 |
| Embodiment 2 | 66.25 | 31.9 | 0.25 | 1.6 | About 2:1 |
| Embodiment 3 | 74.75 | 23.8 | 0.25 | 1.2 | About 3:1 |
| Embodiment 4 | 79.75 | 19.05 | 0.25 | 0.95 | About 4:1 |

Test Example 1

Measuring Net Hardening Time

In order to compare the hardening time of the powder-type dental filling compositions of Embodiments 1 to 4, the following test was carried out according to Annex A of ISO 9917-1:2007(E).

In specific, 1 g of each of the compositions and 0.04 ml of a saline solution were mixed using a spatula, and then the sample was filled in a tetragonal mold with the thickness of 5×2 mm and the length of 10×2 mm. From 90 seconds after the completion of the mixing, the net hardening time was measured using a Gillmore needle with an interval of 30 seconds, and with an interval of up to 10 seconds near the hardening time. Here, the net hardening time was determined by measuring the time elapsed from the completion of the mixing to when the needle fails to penetrate into the cement and form a complete circular impression. The above test was repeated for three times, and the average values are shown in TABLE 2.

TABLE 2

| | Net hardening time (min) |
|---|---|
| Embodiment 1 | 2.5 |
| Embodiment 2 | 2.7 |
| Embodiment 3 | 4.0 |
| Embodiment 4 | 5.3 |

As shown in TABLE 2, it can be seen that due to the inherent acidity of zirconia, the hardening time is increased as the content of zirconia becomes greater.

Test Example 2

Measuring Compressive Strength and Toughness

In order to compare the compressive strength of the powder-type dental filling compositions of Embodiments 1 to 4, the following test was carried out according to Annex D of ISO 9917-1:2007(E).

In specific, 1 g of each of the compositions and 0.04 ml of a saline solution were mixed using a spatula, and then the sample was filled in a mold with the diameter of 4×0.1 mm and the height of 6×0.1 mm within 60 seconds. Within 120 seconds from the mixing, the mold filled with the sample was kept at 37±1° C. for one hour. The sample was taken out after one hour and immersed in water at 37±1° C. for 23±5 hours. After 24 hours elapsed from the mixing of the sample, five specimens kept in distilled water were taken out and the diameters of the specimens were measured using digital calipers. A compression jig was installed in a universal strength tester and the specimen was placed on the center of the jig. Then load was applied at a loading rate of 0.75 mm/min until the specimen was broken, and the compressive strength of each broken specimen was measured. The average values thereof are shown in TABLE 3.

Further, the toughness values were obtained by determining the total areas under stress-strain curves for the above measured values. The results are shown in TABLE 3.

TABLE 3

| | Compressive strength (MPa) | Toughness (J) |
|---|---|---|
| Embodiment 1 | 6.8 | 0.06667 |
| Embodiment 2 | 5.2 | 0.03702 |
| Embodiment 3 | 2.3 | 0.01514 |
| Embodiment 4 | 2.1 | 0.01445 |

As shown in TABLE 3, the compressive strength and toughness is drastically reduced as the content of zirconia is increased, and it can be seen that a problem is caused in which the compositions of Embodiments 2 to 4 containing 66 wt % or more of zirconia may be broken under occlusal pressure due to the drastic reduction in the compressive strength and toughness. Thus, the composition of Embodiment 1 containing about 50 wt % of zirconia may preferably be employed as a base under a filling.

On the other hand, the composition of Embodiment 2 containing about 66 wt % of zirconia may preferably be employed as a sealer for permanent teeth. If the above content is exceeded, the strength becomes excessively low and a problem is caused in which the composition may be taken out together when gutta-percha is removed for a post. Further, the composition of Embodiment 3 or 4 containing about 75 wt % or 80 wt % of zirconia may preferably be employed as a root canal filling material for deciduous teeth, so that it may respond to the eruption pressure of permanent teeth.

Test Example 3

Comparing Radiopacity (Radiodensity)

In order to compare the radiopacity of the powder-type dental filling compositions of Embodiments 1 to 4, the following test was carried out according to Annex H of ISO 9917-1:2007(E).

In specific, 1 g of each of the compositions and 0.04 ml of a saline solution were mixed using a spatula, the sample was then filled in a mold with the diameter of 15.0×0.1 mm and the depth of 1.0×0.1 mm, and a film and a glass plate were covered thereon. When the sample was completely hardened, it was taken out from the mold and made into three specimens with the thickness of 1.0×0.1 mm. The specimen was kept in water at 23±1° C. up to seven days, and taken out from water to measure the optical density thereof within thirty minutes. An X-ray film was placed on a lead plate, and the specimen was placed on the center of the film together with aluminum plates spaced apart by 0.5 mm (i.e., a step wedge ranging from 0.5 to 5.0 mm). An X-ray of 65.5 kV was irradiated with the distance between the object and film being 30 to 40 cm, and the film was exposed for an appropriate time so that the portions of the film around the specimen and aluminum step wedge would have an optical density of 1.5 to 2.0 after development. After the exposed film was developed, fixed and dried, the optical density of the specimen was compared to that of the aluminum step wedge using an optical density meter (i.e., densitometer). The correlation between the optical density and thickness of the aluminum step wedge was plotted into a graph, and then the optical density of the specimen measured by the densitometer was placed onto the Y-axis of the graph to determine the corresponding thickness of the aluminum step wedge ($\delta_a$). The thickness of the specimen was measured as $\delta_s$, and the radiopacity of the specimen was determined as $\delta_a/\delta_s$. The radiopacity was considered to be appropriate if it was equal to or greater than 1 mm. The results are shown in TABLE 4.

TABLE 4

| | Radiopacity ($\delta_a/\delta_s$, mm) |
|---|---|
| Embodiment 1 | 4.25 |
| Embodiment 2 | 4.13 |
| Embodiment 3 | 5.32 |
| Embodiment 4 | 5.65 |

As shown in TABLE 4, it can be seen that the compositions according to the invention exhibit good radiopacity equivalent to or greater than that of aluminum even though they do not contain any heavy metals.

Test Example 4

Measuring pH Change and Ca Ion Release Over Time

In order to compare the pH change and Ca ion release over time of the powder-type dental filling compositions of Embodiments 1 to 4, the following test was carried out according to Annex H of ISO 9917-1:2007(E).

In specific, 1 g of each of the compositions and 0.04 ml of a saline solution were mixed using a spatula, the sample was then filled in a mold with the diameter of 15.0×0.1 mm and the depth of 1.0×0.1 mm, and a film and a glass plate were covered thereon. When the sample was completely hardened, it was taken out from the mold and made into three specimens with the thickness of 1.0×0.1 mm. The specimen was kept in an oven at 37±1° C. for 24 hours, and then immersed in a plastic container containing 10 ml of distilled water. The specimen was taken out after 3 hours to remove moisture therefrom, and was placed in a new container containing 10 ml of distilled water. The above procedure was identically carried out for 6 hours, 12 hours, 1 day, 2 days, 7 days, 14 days and 21 days, thus eight times in total. Upon the completion of the test, the pH of the solution was immediately measured using a pH meter. The calcium ion contained in the solution was quantitatively analyzed through ICP measurement. The average values of the three specimens are shown in TABLE 5 and TABLE 6.

TABLE 5

| | pH | | | | | | | | |
|---|---|---|---|---|---|---|---|---|---|
| | 3 h | 6 h | 12 h | 1 d | 2 d | 7 d | 14 d | 21 d | Change |
| Embodiment 1 | 11.25 | 11.19 | 11.19 | 11.30 | 11.25 | 11.51 | 12.14 | 11.77 | 11.19-12.14 |
| Embodiment 2 | 11.17 | 11.21 | 11.17 | 11.28 | 11.11 | 11.57 | 12.22 | 11.69 | 11.11-12.22 |
| Embodiment 3 | 11.02 | 11.07 | 11.04 | 11.25 | 11.27 | 11.56 | 12.19 | 11.66 | 11.02-12.19 |
| Embodiment 4 | 10.94 | 11.08 | 11.07 | 11.23 | 11.23 | 11.64 | 12.13 | 11.66 | 10.94-12.13 |

TABLE 6

| | Cumulative release of Ca ion (ppm) | | | | | | | |
|---|---|---|---|---|---|---|---|---|
| | 3 h | 6 h | 12 h | 1 d | 2 d | 7 d | 14 d | 21 d |
| Embodiment 1 | 11.42 | 51.31 | 89.68 | 138.17 | 191.99 | 307.59 | 507.47 | 697.68 |
| Embodiment 2 | 21.95 | 57.66 | 95.74 | 136.88 | 182.72 | 296.29 | 450.37 | 592.24 |
| Embodiment 3 | 24.48 | 64.01 | 99.57 | 142.54 | 198.38 | 295.77 | 444.00 | 586.88 |
| Embodiment 4 | 30.64 | 64.24 | 97.94 | 138.77 | 189.64 | 315.48 | 462.34 | 605.39 |

As shown in TABLE 5 and TABLE 6, the composition according to the invention, which employs a weakly acidic material like citric acid or tartaric acid as a hardening control agent and contains a minimum amount of calcium silicate cement, may reduce the amount of highly alkaline calcium hydroxide produced in the hydration process so that the calcification of dental pulp may be suppressed. Therefore, less irritation may be caused in paradental tissues.

Test Example 5

Measuring Micro-Leakage

Twenty pieces of recently extracted single-rooted teeth having no caries were prepared up to Protaper F3. Next, by means of a continuous wave technique, ten pieces of the teeth were filled using the dental filling composition of Embodiment 2 according to the invention as a root canal sealer, and the other ten pieces were filled using AH-26 (from Dentsply, USA) as a root canal sealer. The filled teeth were kept at a humidity of 95% and at 37° C. for 24 hours. Thereafter, nail varnish was twice applied onto the portions of the teeth except for 3 mm of the root ends thereof, and the teeth were kept in a 1% methylene blue solution for seven days. After seven days, the maximum length of micro-leakage in the teeth along the longitudinal axis thereof was measured, and the results are shown in FIG. 1. Here, t-test was used for statistical analysis, and Turkey's test was used for post-hoc analysis.

Figure 2:
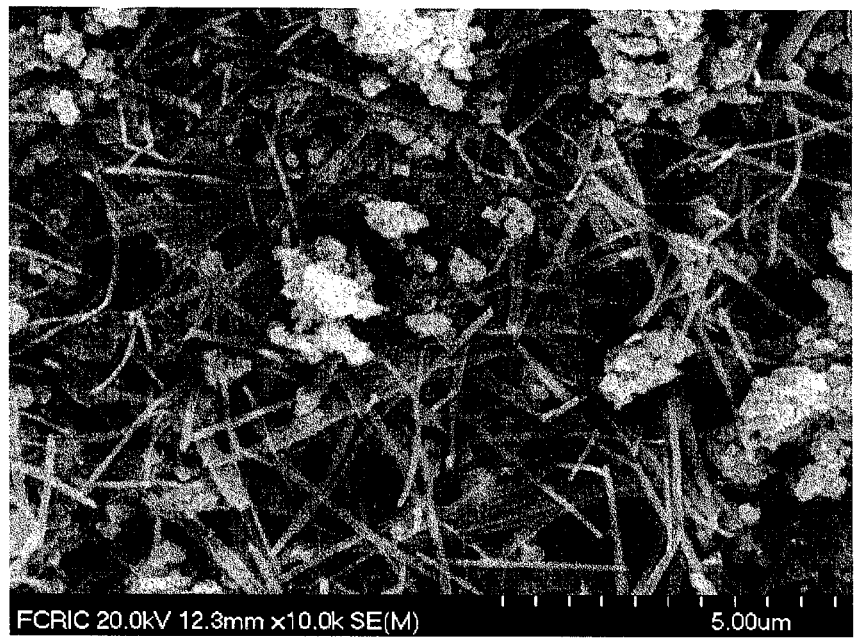
FIGS. 2 and 3 are scanning electron micrographs of a material obtained by mixing with distilled water and hardening the composition of Embodiment 2 according to the invention.
Figure 3:

Further, FIGS. 2 and 3 show the scanning electron micrographs of a material obtained by mixing with distilled water and hardening the composition of Embodiment 2.

As shown in FIGS. 1 to 3, it can be seen that the dental filling composition according to the invention has a relatively uniform structure and excellent sealing property compared to AH-26, which is a most commonly used resin-type sealer.

Test Example 6

Measuring Porosity

In order to compare the porosity of the powder-type dental filling compositions of Embodiments 1 to 4, the compositions of Embodiments 1 to 4 were respectively mixed with distilled water at a ratio of 10:4 and hardened, and then the porosity and the total pore area were measured using an automatic porosimeter (from Micromeritics). The results are shown in TABLE 7.

TABLE 7

|  | Porosity (%) | Total pore area (m$^2$/g) |
| --- | --- | --- |
| Embodiment 1 | 55.9894 | 34.132 |
| Embodiment 2 | 59.3728 | 35.051 |
| Embodiment 3 | 63.3653 | 33.584 |
| Embodiment 4 | 63.8930 | 31.375 |

As shown in TABLE 7, it can be seen that the porosity is increased but the total pore area is decreased as the content of zirconia is increased. In this regard, it can be appreciated that the water-tightness involved with micro-leakage is not significantly varied in the entire range of the compositions according to the invention (i.e., the content of zirconia ranging from 45 to 85%).

What is claimed is:
1. A dental filling composition comprising zirconia powder, wherein the composition comprises the following with respect to the total weight thereof:
   1) 45 to 85% of zirconia powder;
   2) 14 to 54% of a hydraulic inorganic binder, wherein the hydraulic inorganic binder is calcium silicate cement;
   3) 0.5% or less of maleic acid, citric acid, or tartaric acid as a weakly acidic hardening control agent; and
   4) 5% or less of a pozzolan component.
2. The dental filling composition as claimed in claim 1, wherein when the composition is used as a base, the content of the zirconia powder is 45 to 55% and that of the inorganic binder is 44 to 54%, with respect to the total weight of the composition.
3. The dental filling composition as claimed in claim 1, wherein when the composition is used as a sealer for permanent teeth, the content of the zirconia powder is 60 to 70% and that of the inorganic binder is 29 to 39%, with respect to the total weight of the composition.
4. The dental filling composition as claimed in claim 1, wherein when the composition is used for root canal filling of deciduous teeth, the content of the zirconia powder is 70 to 85% and that of the inorganic binder is 14 to 29%, with respect to the total weight of the composition.
5. The dental filling composition as claimed in claim 1, wherein the zirconia powder has an average grain size of 20 µm or less.
6. The dental filling composition as claimed in claim 1, wherein the hydraulic inorganic binder has an average grain size of 3 µm or less.
7. The dental filling composition as claimed in claim 1, wherein the weakly acidic hardening control agent is citric acid.
8. The dental filling composition as claimed in claim 1, wherein the weakly acidic hardening control agent is used in an amount of 0.25% or less with respect to the total weight of the composition.
9. The dental filling composition as claimed in claim 1, wherein the pozzolan component is used in an amount of 3% or less with respect to the total weight of the composition.
10. The dental filling composition as claimed in claim 1, wherein for reaction with the pozzolan, the composition further comprises one or more additives selected from a group consisting of fumed silica, volcanic ash, kaolin, coral powder, and clay silicate.
11. The dental filling composition as claimed in claim 1, wherein the composition is in powder form.

* * * * *